(12) United States Patent
Kasahara et al.

(10) Patent No.: US 11,510,609 B2
(45) Date of Patent: Nov. 29, 2022

(54) MUSCLE MASS ESTIMATION METHOD, MUSCLE MASS ESTIMATION DEVICE, AND STORAGE MEDIUM STORING A MUSCLE MASS ESTIMATION PROGRAM

(71) Applicant: Tanita Corporation, Tokyo (JP)

(72) Inventors: Yasuhiro Kasahara, Tokyo (JP); Miyuki Kodama, Tokyo (JP)

(73) Assignee: TANITA CORPORATION, Tokyo (JP)

( * ) Notice: Subject to any disclaimer, the term of this patent is extended or adjusted under 35 U.S.C. 154(b) by 298 days.

(21) Appl. No.: 16/740,784

(22) Filed: Jan. 13, 2020

(65) Prior Publication Data

US 2020/0146617 A1 May 14, 2020

Related U.S. Application Data

(63) Continuation of application No. PCT/JP2018/022482, filed on Jun. 12, 2018.

(30) Foreign Application Priority Data

Jul. 14, 2017 (JP) .............................. JP2017-138513

(51) Int. Cl.
*A61B 5/00* (2006.01)
*A61B 5/0537* (2021.01)
*A61B 5/107* (2006.01)

(52) U.S. Cl.
CPC .......... *A61B 5/4519* (2013.01); *A61B 5/0537* (2013.01); *A61B 5/1072* (2013.01);
(Continued)

(58) Field of Classification Search
CPC ..... A61B 5/053; A61B 5/0537; A61B 5/1072; A61B 5/107; A61B 5/4869; A61B 5/4872; A61B 5/4519
See application file for complete search history.

(56) References Cited

U.S. PATENT DOCUMENTS

2003/0088197 A1    5/2003  Itagaki
2004/0054298 A1*   3/2004  Masuo ................ A61B 5/0537
                                                 600/547
(Continued)

FOREIGN PATENT DOCUMENTS

JP    H 11188016 A    7/1999
JP    2003199728 A    7/2003
(Continued)

OTHER PUBLICATIONS

Japanese Office Action (w/ English translation) for corresponding JP Application No. 2019-528999, dated Nov. 9, 2021, 9 pages.
(Continued)

*Primary Examiner* — Scott M. Getzow
(74) *Attorney, Agent, or Firm* — Dority & Manning, P.A.

(57) ABSTRACT

A muscle mass estimation method including acquiring a height of a living organism, acquiring an electrical resistance value measured for the living organism, and computing a muscle mass of the living organism using a calculation formula including a first variable including the height of the living organism and the electrical resistance value, and a second variable including the electrical resistance value.

11 Claims, 11 Drawing Sheets

(52) U.S. Cl.
    CPC .......... *A61B 5/7246* (2013.01); *A61B 5/7278* (2013.01); *A61B 2562/0252* (2013.01); *A61B 2562/066* (2013.01)

(56) References Cited

U.S. PATENT DOCUMENTS

| | | |
|---|---|---|
| 2004/0082877 A1 | 4/2004 | Kouou et al. |
| 2005/0004491 A1 | 1/2005 | Shiokawa et al. |
| 2007/0233523 A1 | 10/2007 | Izumi |
| 2010/0198100 A1 | 8/2010 | Oku et al. |

FOREIGN PATENT DOCUMENTS

| | | |
|---|---|---|
| JP | 2004141223 A | 5/2004 |
| JP | 2004344518 A | 12/2004 |
| JP | 2007007445 A | 1/2007 |
| JP | 2007260210 | 10/2007 |
| JP | 2009022515 | 2/2009 |
| JP | 2017023311 | 2/2017 |

OTHER PUBLICATIONS

Sakamoto, et al., "Measurement of body fat to bioelectrical impedance analysis," *Japan Society of Ningen Dock*, Oct. 1993, pp. 38-41.
Janssen et al., "Estimation of skeletal muscle mass by bioelectrical impedance analysis," *J. Appl. Physiol.*, vol. 89, 2000, pp. 465-471.
International Search Report for PCT/JP2018/022482 dated Aug. 14, 2018, 2 pages.
Japanese Office Action (w/ English translation) for corresponding Japanese Application No. 2019-528999, dated Jun. 28, 2022, 6 pages.

\* cited by examiner

MUSCLE MASS ESTIMATION METHOD, MUSCLE MASS ESTIMATION DEVICE, AND STORAGE MEDIUM STORING A MUSCLE MASS ESTIMATION PROGRAM

CROSS-REFERENCE TO RELATED APPLICATIONS

This application is a continuation application of International Application No. PCT/JP2018/022482, filed Jun. 12, 2018, the disclosure of which is incorporated herein by reference in its entirety, and which claims priority from Japanese Patent Application No. 2017-138513, filed Jul. 14, 2017.

BACKGROUND

Technical Field

The present invention relates to a muscle mass estimation method, a muscle mass estimation device, and a muscle mass estimation program.

Related Art

Body composition information (muscle mass, body water percentage, body fat percentage, etc.) has hitherto been estimated using bioelectrical impedance analysis (BIA) (see for example non-patent document 1).

In such bioelectrical impedance analysis, the body composition information is computed using a variable obtained by correcting an electrical resistance value such as impedance Z or resistance R for height Ht or body weight Wt.

For example, a variable H1 employed in order to derive muscle mass, body water percentage, or the like can be expressed as in the following equation.

$$H1 = Ht^2/Z \quad (1)$$

Moreover, a variable H2 employed in order to derive the body fat percentage or the like can be expressed as in the following equation.

$$H2 = Ht^2/(Wt \times Z) \quad (2)$$

Moreover, non-patent document 2 gives the following equation as a calculation formula in which the above variables are applied in order to estimate muscle mass (skeletal muscle mass) SM mass.

$$SM\ mass\ (kg) = [(Ht^2/R \times 0.41) + (gender \times 3.825) + \{age \times (-0.071)\}] + 5.102 \quad (3)$$

Here, gender refers to biological sex, with male denoted 1 and female denoted 0. Age is given in years.

Non-patent document 1: Measurement of body fat by bioelectrical impedance analysis, Yoichi SAKAMOTO, Miyuki NISHISAWA, Tomio SATŌ, Makoto ŌNO, Yoshio IKEDA, Japan Society of Ningen Dock, October 1993, pp 38-41.

Non-patent document 2: Estimation of skeletal muscle mass by bioelectrical impedance analysis, Journal of Applied Physiology, online http://jap.physiology.org/content/89/2/465.short (retrieved Jul. 5, 2017).

However, in Equation 3, the single resistance R is employed alone as a variable of the electrical resistance value. The accuracy of the estimated muscle mass cannot be said to be high. Moreover, diurnal fluctuations in the resistance R may result in large diurnal fluctuations in the muscle mass computed using Equation 3.

SUMMARY

An object of the present invention is to provide a muscle mass estimation method, a muscle mass estimation device, and a muscle mass estimation program capable of accurately estimating muscle mass.

In order to address the above issue, a muscle mass estimation method according to a first aspect of the present invention includes acquiring a height of a living organism, acquiring an electrical resistance value measured for the living organism, and computing a muscle mass of the living organism using a calculation formula that includes a first variable including the height of the living organism and the electrical resistance value, and a second variable including the electrical resistance value.

In a second aspect of the present invention, the second variable is a variable that acts in a direction to suppress fluctuation in a computed value correlating with the muscle mass and computed by a term including the first variable in the calculation formula.

In a third aspect of the present invention, in cases in which the electrical resistance value included in the first variable and the electrical resistance value included in the second variable are both included in a denominator or both included in a numerator, a sign of the second variable is opposite to a sign of the first variable, and in cases in which one out of the electrical resistance value included in the first variable or the electrical resistance value included in the second variable is included in a denominator and the other out of the electrical resistance value included in the first variable or the electrical resistance value included in the second variable is included in a numerator, a sign of the second variable is the same sign as a sign of the first variable.

In a fourth aspect of the present invention, part of the first variable is configured by the square of the height divided by the electrical resistance value, part of the second variable is configured by the reciprocal of the electrical resistance value, and a sign of the first variable is opposite to a sign of the second variable.

In a fifth aspect of the present invention, part of the first variable is configured by the square of the height divided by the electrical resistance value, part of the second variable is configured by the electrical resistance value, and a sign of the first variable is the same as a sign of the second variable.

In a sixth aspect of the present invention, part of the first variable is configured by the electrical resistance value divided by the square of the height, part of the second variable is configured by the reciprocal of the electrical resistance value, and a sign of the first variable is the same as a sign of the second variable.

In a seventh aspect of the present invention, part of the first variable is configured by the electrical resistance value divided by the square of the height, part of the second variable is configured by the electrical resistance value, and a sign of the first variable is opposite to a sign of the second variable.

An eighth aspect of the present invention includes acquiring a body weight of the living organism, selecting the calculation formula from out of plural different calculation formulae according to the height and the body weight, and computing the muscle mass of the living organism using the selected calculation formula.

A muscle mass estimation device according to a ninth aspect of the present invention includes a height acquisition section that acquires a height of a living organism, an electrical resistance value acquisition section that acquires an electrical resistance value measured for the living organism, and a computation section that computes a muscle mass of the living organism using a calculation formula including a first variable including the height of the living organism and the electrical resistance value, and a second variable including the electrical resistance value.

A muscle mass estimation program according to a tenth aspect of the present invention is a muscle mass estimation program for causing a computer to execute processing, the processing including acquiring a height of a living organism, acquiring an electrical resistance value measured for the living organism, and computing a muscle mass of the living organism using a calculation formula that includes a first variable including the height of the living organism and the electrical resistance value, and a second variable including the electrical resistance value.

Advantageous Effects of Invention

The present invention exhibits the advantageous effect of enabling muscle mass to be accurately estimated.

DESCRIPTION OF EMBODIMENTS

Explanation follows regarding an exemplary embodiment of the present invention. In the present exemplary embodiment, a muscle mass estimation device according to the present invention is applied to a body composition scale capable of measuring biometric information such as body weight and the body fat percentage.

Figure 1:
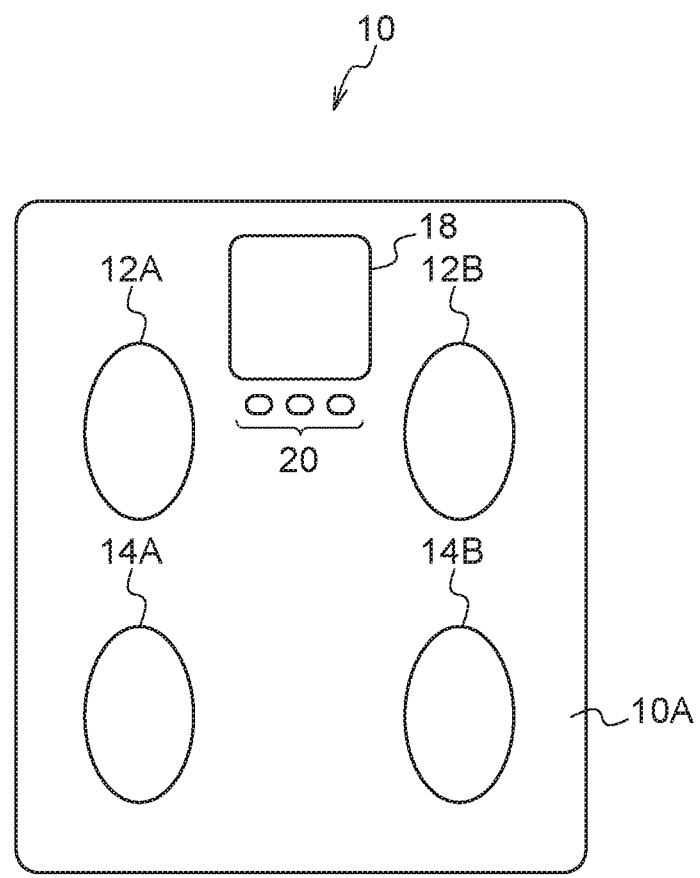
FIG. 1 is a plan view of a body composition scale.
Figure 2:
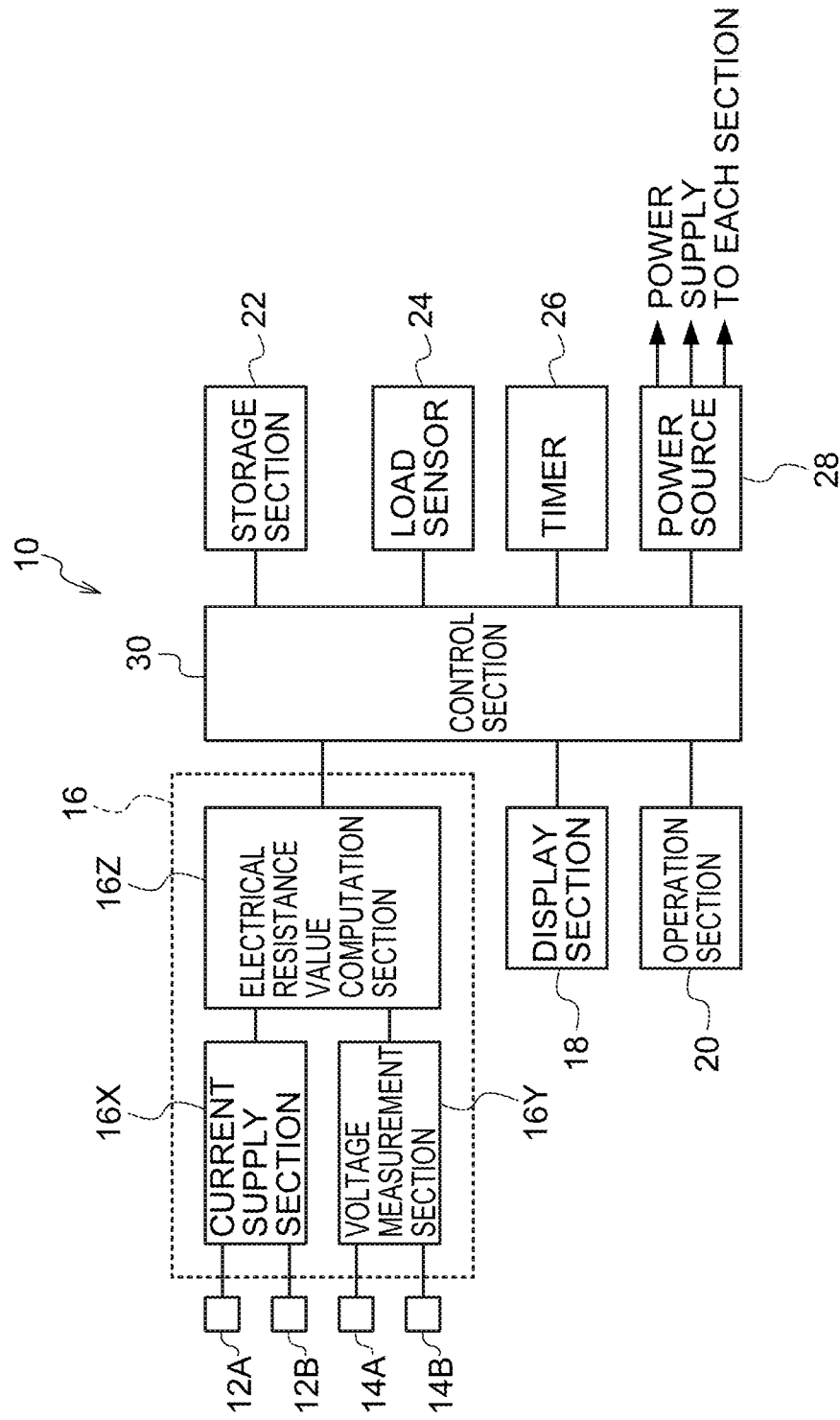
FIG. 2 is a block diagram of a body composition scale.

FIG. 1 is a plan view of a body composition scale 10 according to the present exemplary embodiment. FIG. 2 is a block diagram illustrating configuration of an electrical system of the body composition scale 10.

As illustrated in FIG. 1 and FIG. 2, the body composition scale 10 includes current-applying electrodes 12A, 12B, measurement electrodes 14A, 14B, an electrical resistance value measurement section 16, a display section 18, an operation section 20, a storage section 22, a load sensor 24, a timer 26, a power source 28, and a control section 30.

The electrical resistance value measurement section 16 includes a current supply section 16X, a voltage measurement section 16Y, and an electrical resistance value computation section 16Z.

The current supply section 16X supplies a high frequency alternating current to the current-applying electrodes 12A, 12B.

The voltage measurement section 16Y measures voltage between the measurement electrodes 14A, 14B.

The electrical resistance value computation section 16Z computes an electrical resistance value based on a current value of the alternating current supplied by the current supply section 16X and a voltage value of the voltage measured by the voltage measurement section 16Y. Note that the electrical resistance value may be impedance, or may be resistance.

As illustrated in FIG. 1, four thin plate shaped electrodes configuring the current-applying electrodes 12A, 12B and the measurement electrodes 14A, 14B are disposed spaced apart from each other on a measurement stand 10A of the body composition scale 10. When a user stands on the body composition scale 10, the toes of their left foot contact the current-applying electrode 12A, the heel of their left foot contacts the measurement electrode 14A, the toes of their right foot contact the current-applying electrode 12B, and the heel of their right foot contacts the measurement electrode 14B.

The current-applying electrodes 12A, 12B are connected to the current supply section 16X and configure electrodes for supplying the alternating current used to measure the electrical resistance value along a route passing from the left foot of the user in contact with the current-applying electrode 12A, through the body of the user, and as far as the right foot of the user in contact with the current-applying electrode 12B (or a route passing in the opposite direction thereto). The measurement electrodes 14A, 14B are connected to the voltage measurement section 16Y, and configure electrodes for measuring the voltage between the left foot of the user in contact with the measurement electrode 14A and the right foot of the user in contact with the measurement electrode 14B when the alternating current is being supplied.

An alternating current supplied from the current supply section 16X is supplied into the body of the user through the current-applying electrodes 12A, 12B, and the voltage is measured by the voltage measurement section 16Y through the measurement electrodes 14A, 14B. The electrical resistance value computation section 16Z computes the electrical resistance value of the user based on the respective current and voltage values, and outputs the computed resistance value to the control section 30. The control section 30 enters the measured electrical resistance value, a measured body weight, and user information such as age, gender, and height input by the user into a prescribed calculation formula to compute body composition information such as muscle mass (appendicular skeletal muscle mass), body fat percentage, and visceral fat level. A similar configuration to that of a known body composition scale may be employed as the configuration used to measure the electrical resistance value.

For example, a liquid crystal display (LCD) device may be employed as the display section 18 that displays the measured biometric information and so on.

The operation section 20 is configured including plural operation buttons which function as input buttons for inputting user information such as height, gender, and age, a start button for activating the body composition scale 10, a setting button for activating a setting mode, this being a mode to perform initial settings of the body composition scale 10, and a switch button for switching the displayed measurement result item. Note that the display section 18 and the operation section 20 may be configured as a touch panel that can be operated by directly touching the screen.

The storage section 22 is for example configured by non-volatile memory using semiconductor elements. In addition to user information, the storage section 22 stores results of processing by the control section 30, various data for performing this processing, and so on.

In the present exemplary embodiment as an example, the load sensor 24 employs a load cell. The load cell is configured by a flexure element, this being a metal member that deforms in response to load, and a strain gauge attached to the flexure element. When the user stands on the body composition scale 10, the flexure element of the load sensor 24 flexes under the load from the user, the strain gauge extends or contracts, and a resistance value (output value) of the strain gauge alters according to this extension or contraction.

The control section 30 computes body weight by computing the difference between an output value (zero) of the load sensor 24 when load is not applied and an output value when load is applied, and thereby measures the body weight of the user. A similar configuration to that of a known body weight scale may be employed as the configuration to measure body weight using the load sensor 24.

Figure 3:
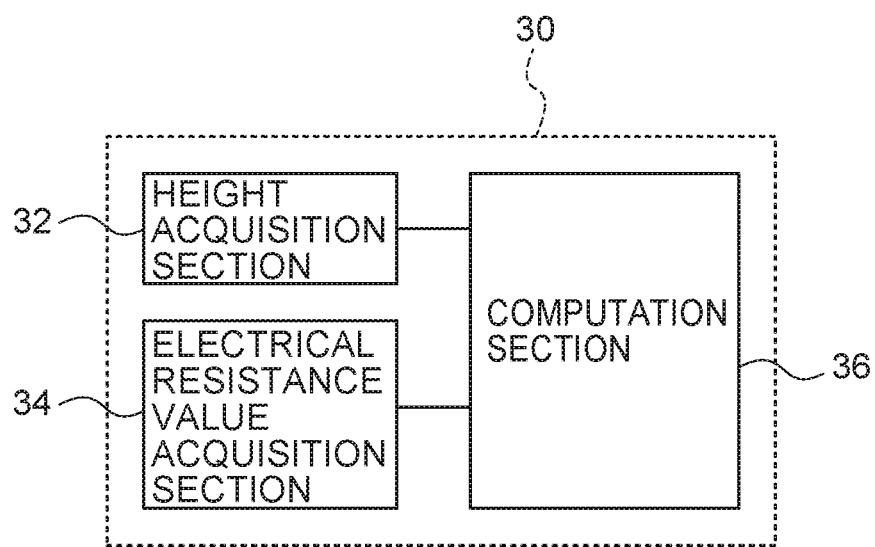
FIG. 3 is a functional diagram of a control section.

The control section 30 also functions as a muscle mass estimation device according to the present invention. As illustrated in FIG. 3, in terms of functionality, the control section 30 includes a height acquisition section 32, an electrical resistance value acquisition section 34, and a computation section 36.

The height acquisition section 32 reads the height of the user from the storage section 22 to acquire the height of the user.

The electrical resistance value acquisition section 34 acquires the electrical resistance value measured for the user from the electrical resistance value measurement section 16.

The computation section 36 computes the muscle mass of the user using a calculation formula that includes a first variable including the height of the user and the electrical resistance value, and a second variable including the electrical resistance value. Note that this calculation formula will be described in detail later.

The timer 26 includes a function to acquire the current time and a time-measuring function to measure a set duration.

The power source 28 converts a voltage supplied from a non-illustrated battery or commercial power source to a prescribed voltage, and supplies this voltage to the various functional sections configuring the body composition scale 10.

In terms of hardware configuration, the control section 30 is configured including a CPU, ROM, RAM, and the like, none of which are illustrated in the drawings. A muscle mass estimation program used by the CPU to execute muscle mass estimation processing, described later, is stored in the ROM. The CPU reads the muscle mass estimation program from the ROM and executes the muscle mass estimation program. Note that the muscle mass estimation program may be provided on a recording medium such as a CD-ROM or a memory card, or may be downloaded from a non-illustrated server.

The control section 30 may for example be a dedicated device, or may be a generic information processing device such as a personal computer, a smartphone, a cellphone, or a tablet.

Figure 4:
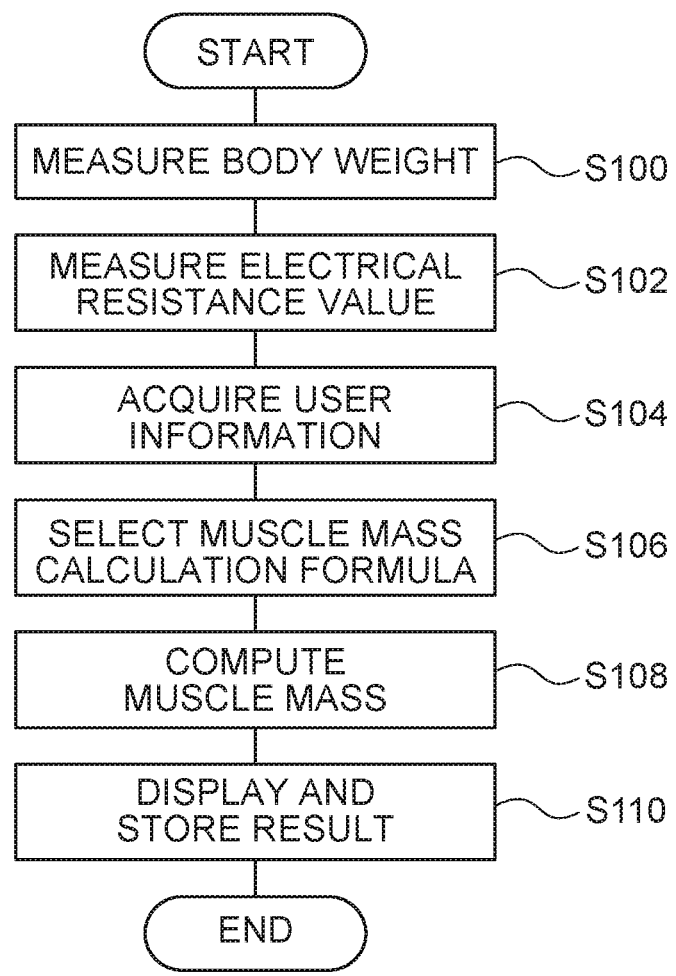
FIG. 4 is a flowchart of processing by a muscle mass estimation program.

Explanation follows regarding muscle mass estimation processing as operation of the present exemplary embodiment, with reference to the flowchart illustrated in FIG. 4. The muscle mass estimation processing is performed by the control section 30 executing the muscle mass estimation program. Note that the processing illustrated in FIG. 4 is executed when a user standing on the body composition scale 10 has been detected.

At step S100, the body weight of the user is measured. Specifically, an output value of the load sensor 24 is acquired, and the body weight is derived by calculating the difference between the acquired output value of the load sensor 24 and an output value (zero) of the load sensor 24 when not applied with load.

At step S102, the electrical resistance value of the user is measured. Specifically, the electrical resistance value measurement section 16 is instructed to measure the electrical resistance value. The current supply section 16X supplies the alternating current for measuring the electrical resistance value to the current-applying electrodes 12A, 12B. The voltage between the measurement electrodes 14A, 14B is then measured by the voltage measurement section 16Y, and the electrical resistance value is computed by the electrical resistance value computation section 16Z.

Note that when estimating muscle mass, a frequency in for example a range from 5 kHz to 250 kHz is selected as the frequency of the alternating current. As described in detail later, different frequencies are selected depending on the calculation formula used to compute muscle mass.

The control section 30 acquires the electrical resistance value of the user as computed by the electrical resistance value computation section 16Z.

At step S104, user information is acquired. Namely, user information such as height, age, and gender stored in the storage section 22 is read.

At step S106, a calculation formula to be employed to estimate muscle mass is selected. Note that these calculation formulae will be described in detail later.

At step S108, the muscle mass is computed using the calculation formula selected at step S106. Note that this computation of the muscle mass will be described in detail later.

Note that in addition to computing muscle mass, biometric information such as the body fat percentage, visceral fat level, basal metabolic rate, estimated bone mass, and body water percentage may also be computed at step S108. The biometric information such as the body fat percentage, visceral fat level, basal metabolic rate, estimated bone mass, and body water percentage are derived by entering the electrical resistance value measured by the electrical resistance value measurement section 16, the user information such as age, gender, and height stored in the storage section 22, and the body weight measured at step S100 into a calculation formula prescribed according to the biometric information, and performing a computation.

At step S110, the muscle mass computed at step S108 using the calculation formula selected at step S106 is displayed on the display section 18 and stored in the storage section 22. Note that when other biometric information such as the body fat percentage, visceral fat level, basal metabolic rate, estimated bone mass, and body water percentage has been computed in addition to computing the muscle mass at step S108, this other biometric information is also displayed on the display section 18 and stored in the storage section 22.

Detailed explanation follows regarding the calculation formula employed in estimating muscle mass.

In the present exemplary embodiment, the muscle mass of the user is computed using a calculation formula that includes the first variable including the height of the user acquired at step S104 and the electrical resistance value measured at step S102, and the second variable including the electrical resistance value measured at step S102.

In the present exemplary embodiment, as an example muscle mass is denoted M, the height of the user is denoted Ht, the electrical resistance value is denoted Z, the first variable is denoted X1, and the second variable is denoted X2. The first variable X1 is a variable including $Ht^2/Z$ or $Z/Ht^2$. Namely, part of the first variable X1 is configured by the square of the height Ht divided by the impedance Z, or is configured by the impedance Z divided by the square of the height Ht. The second variable X2 is a variable including Z or 1/Z. Namely, part of the second variable X2 is configured by the impedance Z, or is configured by the reciprocal of the impedance Z. Note that the first variable X1 and the second variable X2 may also include other variables such as body weight.

Explanation follows regarding the first variable X1.

Muscle may be regarded as an electrical conductor including a specific amount of water. For example, a human muscle may be considered to be a circular column shaped electrical conductor with a cross-section area of A and a length of L, with an electrical conductivity of the conductor being σ. Note that electrical conductivity is a physical quantity indicating the ease with which electricity passes through.

Where Z is impedance, the impedance Z is inversely proportional to the cross-section area A and proportional to the length L. The impedance Z can thus be expressed as in Equation 4.

$$Z = 1/\sigma \times L/A \qquad (4)$$

Equation 4 can be rearranged in terms of the cross-section area A as expressed in Equation 5.

$$A = 1/\sigma \times L/Z \qquad (5)$$

Where V is a volume of the conductor, the volume V can be expressed as in Equation 6 based on Equation 5.

$$\begin{aligned} V &= L \times A \\ &= L \times (1/\sigma \times L/Z) \\ &= 1/\sigma \times L^2/Z \end{aligned} \qquad (6)$$

In the human body, the values of the impedance Z and resistance R are close to each other and are very closely correlated. Thus, Equation 6 may be expressed in the manner of Equation 7.

$$V = 1/\sigma \times L^2/R \qquad (7)$$

The first variable X1 may thus be said to be a variable relating to volume. If length information such as the height Ht and an electrical resistance value such as the impedance Z can be obtained, the muscle mass can be estimated. Namely, a term including the first variable X1 in the calculation formula to compute the muscle mass of the user is used to compute a value correlated with the muscle mass.

Next, explanation follows regarding the variable X2.

Hitherto, the electrical conductivity σ in Equation 7 would normally have been set to a fixed value. However, in reality, the electrical conductivity σ varies from person to person. Thus, errors are more likely to arise in the case of people with higher muscle water content, people prone to dehydration, and so on.

As previously described, the electrical conductivity σ indicates the ease with which electricity passes through, and is known to be inversely proportional to the impedance Z. Thus, in the present exemplary embodiment, as an example Z or 1/Z is adopted as the variable X2 relating to electrical conductivity and used as a correction variable. This enables the muscle mass to be accurately estimated.

Moreover, by computing the muscle mass using a calculation formula including both the first variable X1 including $Ht^2/Z$ or $Z/Ht^2$ as the first variable X1 relating to volume and the second variable X2 including Z or 1/Z as the variable X2 relating to electrical conductivity, the influence of diurnal fluctuations in the impedance Z can be suppressed, enabling the muscle mass to be accurately computed. Note that diurnal fluctuations in the impedance Z occur due to for example diurnal fluctuations in water content.

Specifically, Equation 8 may be employed as a calculation formula to compute muscle mass ASM.

$$ASM = a + b \times (X1) + c \times (X2) \qquad (8)$$

Note that a, b, and c are constants. The constants a, b, and c are set in advance based on, for example, results of measuring the muscle mass of multiple test subjects. The first variable X1 and the second variable X2 are variables including arithmetic signs.

Specifically, Equation 8 may be expressed as in Equations 9, 10, 11, and 12 below.

$$ASM = a + b \times (Ht^2/Z) + c \times (-1/Z) \qquad (9)$$

$$ASM = a + b \times (Ht^2/Z) + c \times (Z) \qquad (10)$$

$$ASM = a + b \times (-Z/Ht^2) + c \times (-1/Z) \qquad (11)$$

$$ASM = a + b \times (-Z/Ht^2) + c \times (Z) \qquad (12)$$

The second variable X2 is a variable that acts to suppress fluctuations in the computed value correlated to the muscle mass ASM computed using Equation 8 by suppressing fluctuations in the first variable X1. Thus, in cases in which the impedance value Z included in the first variable X1 and the impedance value Z included in the second variable X2 are both included in a denominator or both included in a numerator, the sign of the second variable X2 is opposite to the sign of the first variable X1. In contrast thereto, in cases in which one out of the impedance value Z included in the first variable X1 or the impedance value Z included in the second variable X2 is included in a denominator, and the other thereof is included as a numerator, the sign of the second variable X2 is the same as the sign of the first variable X1. This enables the influence of diurnal fluctuations in the impedance Z of the user to be suppressed, and the muscle mass to be accurately estimated.

Explanation follows regarding this point, using an example in which the muscle mass is computed employing Equation 9. Supposing the electrical resistance value, for example the impedance Z, has fluctuated from 500Ω to 450Ω after bathing. In Equation 9, the impedance Z is included in a denominator in the first variable X1, and so the post-fluctuation first variable X1 is greater than the pre-fluctuation first variable X1. Thus, as a result of the impedance Z fluctuating from 500Ω to 450Ω, a computed value correlated to muscle mass ASM and computed using the term including the first variable X1 would increase.

However, in Equation 9, the impedance Z is also included in a denominator in the second variable X2, and so the post-fluctuation second variable X2 is greater than the pre-fluctuation second variable X2. Moreover, the sign of the second variable X2 is the opposite of the sign of the first variable X1. Thus, the second variable X2 acts to reduce the increase caused by the impedance Z fluctuating from 500Ω to 450Ω in the computed value correlated to the muscle mass ASM and computed using the term including the first variable X1. The muscle mass ASM computed using Equation 9 is thereby a value in which fluctuations are suppressed. This enables the influence of diurnal fluctuations in the electrical resistance value to be suppressed and the muscle mass to be accurately computed.

Explanation follows regarding a relationship between the first variable X1 and the muscle mass ASM, and a relationship between the second variable X2 and body weight.

Figure 5:
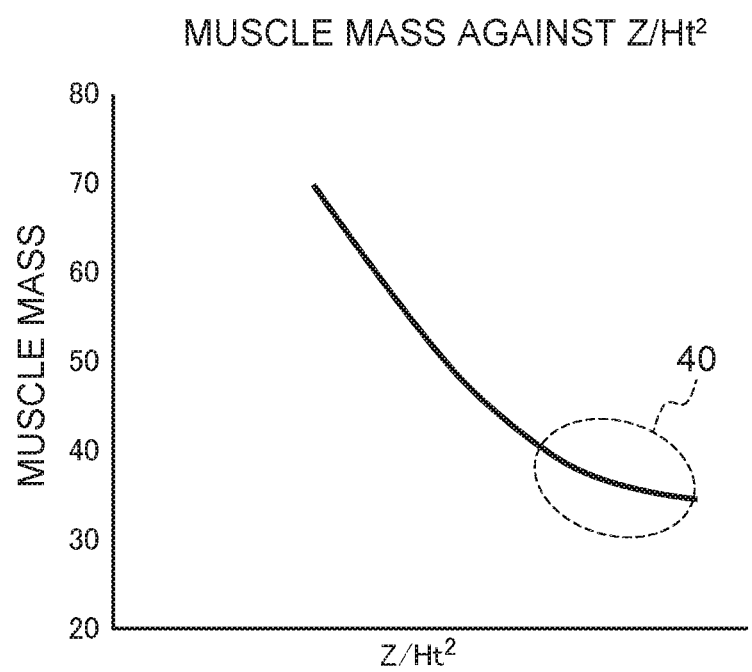
FIG. 5 is a graph illustrating a relationship between a first variable and muscle mass.
Figure 6:
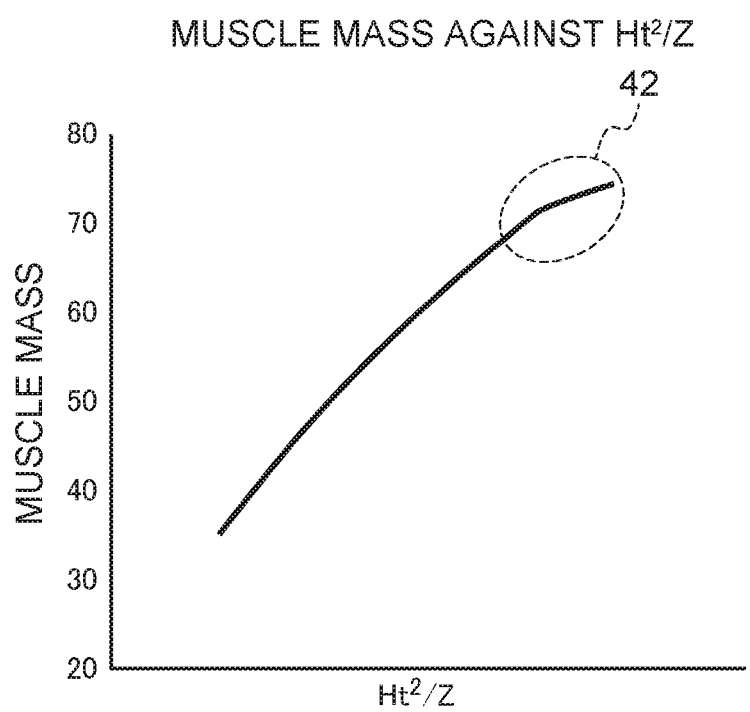
FIG. 6 is a graph illustrating a relationship between a first variable and muscle mass.

FIG. 5 illustrates a relationship between the first variable X1 and the muscle mass ASM in a case in which $Z/Ht^2$ is taken as the first variable X1. FIG. 6 illustrates a relationship between the first variable X1 and the muscle mass ASM in a case in which $Ht^2/Z$ is taken as the first variable X1.

As illustrated in FIG. 5, in the case in which $Z/Ht^2$ is taken as the first variable X1, a substantially linear change in the muscle mass ASM is obtained in response to a change in the first variable X1 ($Z/Ht^2$). However, as the first variable X1 ($Z/Ht^2$) becomes larger, the linearity between the change in the muscle mass ASM and the change in the first variable X1 ($Z/Ht^2$) breaks down. For example, in the region labeled region 40, the rate of change of the muscle mass ASM with respect to the change in the first variable X1 ($Z/Ht^2$) is smaller than in other regions. The first variable X1 ($Z/Ht^2$) in this case is a variable that increases as the height Ht decreases. Namely, there tends to be an increasing difference arising due to the size of the impedance Z when muscle mass is computed for people of short height falling in the region 40 than when muscle mass is computed for people of taller height falling in the region 40.

As illustrated in FIG. 6, in the case in which $Ht^2/Z$ is taken as the first variable X1, a substantially linear change in the muscle mass ASM is obtained from a change in the first variable X1 ($Ht^2/Z$). However, as the first variable X1 ($Ht^2/Z$) becomes larger, the linearity between the change in the muscle mass ASM and the change in the first variable X1 ($Ht^2/Z$) breaks down. For example, in the region labeled region 42, the rate of change of the muscle mass ASM with respect to the change in the first variable X1 ($Ht^2/Z$) is smaller than in other regions. The first variable X1 ($Ht^2/Z$) in this case is a variable that increases as the height Ht increases. There tends to be an increasing difference arising due to the size of the impedance Z when muscle mass is computed for people of tall height falling in the region 42 than when muscle mass is computed for people of shorter height falling in the region 42.

Figure 7:
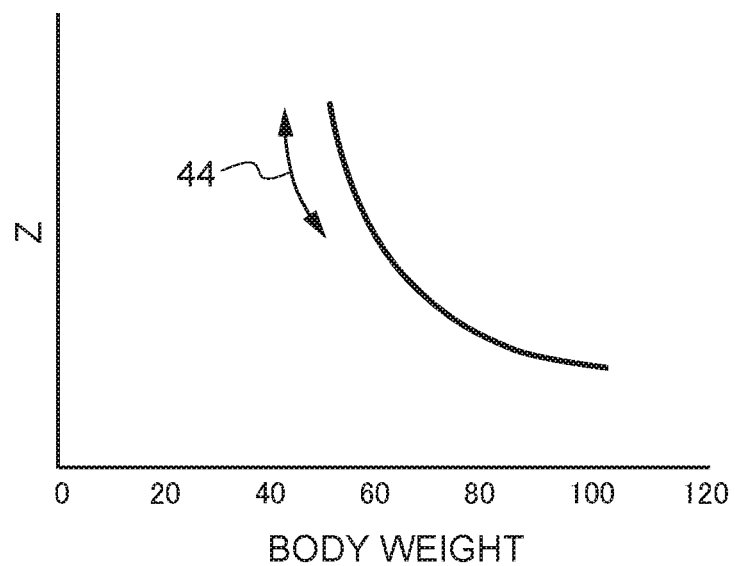
FIG. 7 is a graph illustrating a relationship between body weight and an electrical resistance value.
Figure 8:
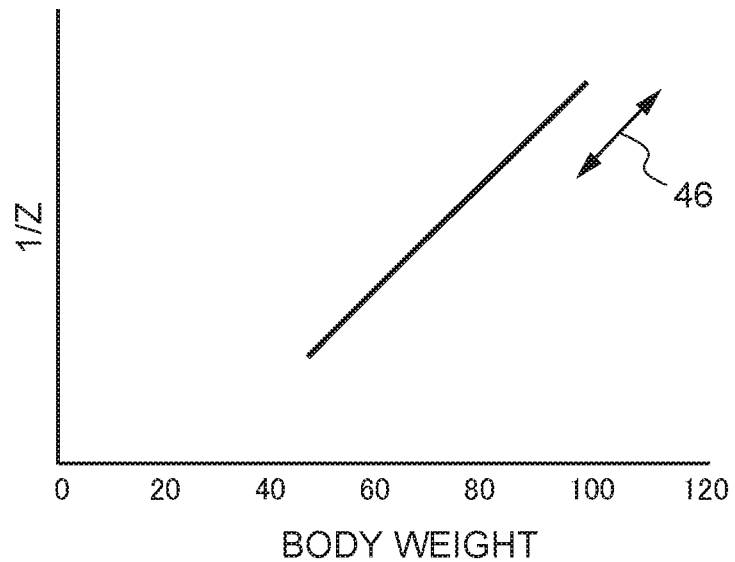
FIG. 8 is a graph illustrating a relationship between body weight and an electrical resistance value.

FIG. 7 illustrates a relationship between the second variable X2 and body weight in a case in which Z is taken as the second variable X2. FIG. 8 illustrates a relationship between the second variable X2 and body weight in a case in which 1/Z is taken as the second variable X2.

As illustrated in FIG. 7, change in the impedance Z with respect to change in body weight increases as the body weight becomes lighter. Thus, in the case in which Z is taken as the second variable X2 as illustrated in FIG. 7, for people with a light body weight falling in a region 44 even a slight change in body weight due to for example a change in water content might lead to a large change in a value computed using the term including the second variable X2.

As illustrated in FIG. 8, in the case in which 1/Z is taken as the second variable X2, a change in body weight results in a substantially linear change in the second variable X2 (1/Z). In general, the heavier the body weight, the greater the fluctuations in body weight. Thus, people with a heavy body weight such as those falling in a region 46 tend to experience greater diurnal fluctuations in body weight than people with lighter body weights than those falling in the region 46, and so the second variable X2 (1/Z) would tend to undergo greater diurnal fluctuations.

Due to the above, $Ht^2/Z$ is preferably adopted as the first variable X1 in cases in which, for example, measurement subjects for muscle mass ASM are in a group that does not include anyone of unusually tall height. Thus, in cases in which the measurement subjects for muscle mass ASM are a group that does not include anyone of unusually tall height, for example in cases in which nationality and ethnicity can be identified, for example as "Japanese", the muscle mass ASM is preferably computed using Equation 9 or Equation 10. Further, in cases in which people of comparatively light body weight are included in the group of people that does not include anyone of unusually tall height, the muscle mass ASM is preferably computed using Equation 10. Conversely, in cases in which people of comparatively heavy body weight are included amongst people that do not have an unusually tall height, the muscle mass ASM is preferably computed using Equation 9.

Moreover, $Z/Ht^2$ is preferably adopted as the first variable X1 in cases in which the measurement subjects for muscle mass ASM are in a group that does not include anyone of small build. Thus, in cases in which it can be identified that people of small build are not present, for example as in the case of participants of a particular sport, the muscle mass ASM is preferably computed using Equation 11 or Equation 12. Further, in cases in which people of comparatively light body weight are included in the group of people that does not include anyone of small build, the muscle mass ASM is preferably computed using Equation 12. Conversely, in cases in which people of comparatively heavy body weight are included in the group of people that does not include anyone of small build, the muscle mass ASM is preferably computed using Equation 11.

In cases in which the measurement subjects for muscle mass ASM are a group consisting of a broad range of people from those of small build to those of unusually tall height, one equation out of Equation 9, 10, 11, or 12 is preferably selected according to the height and body weight of each user.

Specifically, for example, a threshold value TA1 for determining whether or not a person is of unusually tall height, and a threshold value TA2 (<TA1) for determining whether or not a person is of small build, are set in advance. A threshold value TB for determining whether a person has a comparatively light body weight or a comparatively heavy body weight is also set in advance.

In cases in which the height of the user acquired at step S104 is less than the threshold value TA1 and the body weight of the user measured at step S100 is the threshold value TB or greater, Equation 9 is selected.

In cases in which the height of the user acquired at step S104 is less than the threshold value TA1 and the body weight of the user measured at step S100 is less than the threshold value TB, Equation 10 is selected.

In cases for example in which the height of the user acquired at step S104 is the threshold value TA2 or greater and the body weight of the user measured at step S100 is the threshold value TB or greater, Equation 11 may be selected.

In cases in which the height of the user acquired at step S104 is the threshold value TA2 or greater and the body weight of the user measured at step S100 is less than the threshold value TB, Equation 12 may be selected.

Alternatively, the calculation formula used to compute the muscle mass ASM may be selected by employing a table in which the user height acquired at step S104 and the user body weight acquired at step S100 are associated with the calculation formula of one out of the Equations 9, 10, 11, or 12.

Selecting a calculation formula appropriate to the height and body weight of the user in this manner enables the muscle mass ASM to be accurately computed.

At step S108, the electrical resistance value Z measured at step S102 and the height Ht of the user acquired at step S104 are entered into the calculation formula selected at step S106 to compute the muscle mass ASM.

At step S110, the muscle mass ASM computed at step S108 is displayed on the display section 18 and stored in the storage section 22.

In this manner, in the present exemplary embodiment the muscle mass is computed using a calculation formula including both the first variable X1 relating to volume and the second variable X2 relating to electrical conductivity, and in which the sign of the first variable X1 and the sign of the second variable X2 are opposite to each other. This enables the influence of diurnal fluctuations in muscle mass to be suppressed and the muscle mass to be accurately computed.

Explanation follows regarding an example of the present invention.

The inventors tested the accuracy of the muscle mass obtained in cases in which the muscle mass was computed using a calculation formula employing only the first variable X1 ($Ht^2/Z$) (hereafter Formula A), and in cases in which muscle mass was computed using a calculation formula employing both the first variable X1 ($Ht^2/Z$) and the second variable X2 (1/Z), namely, Equation 9 (hereafter, Formula B).

The respective averages (Ave), standard deviations (SD), maximum values (MAX), and minimum values (MIN) of the ages (Age), heights (Ht), body weights (Wt), BMI, and muscle mass ASM of the test subjects (97 people) are given below.

TABLE 1

|  | Age | Ht | Wt | BMI |
|---|---|---|---|---|
| Ave | 48.5 | 167.0 | 67.0 | 24.0 |
| SD | 17.7 | 7.6 | 10.4 | 3.1 |
| MAX | 78.0 | 184.6 | 99.0 | 30.1 |
| MIN | 18.0 | 150.0 | 47.3 | 17.6 |

Figure 9:
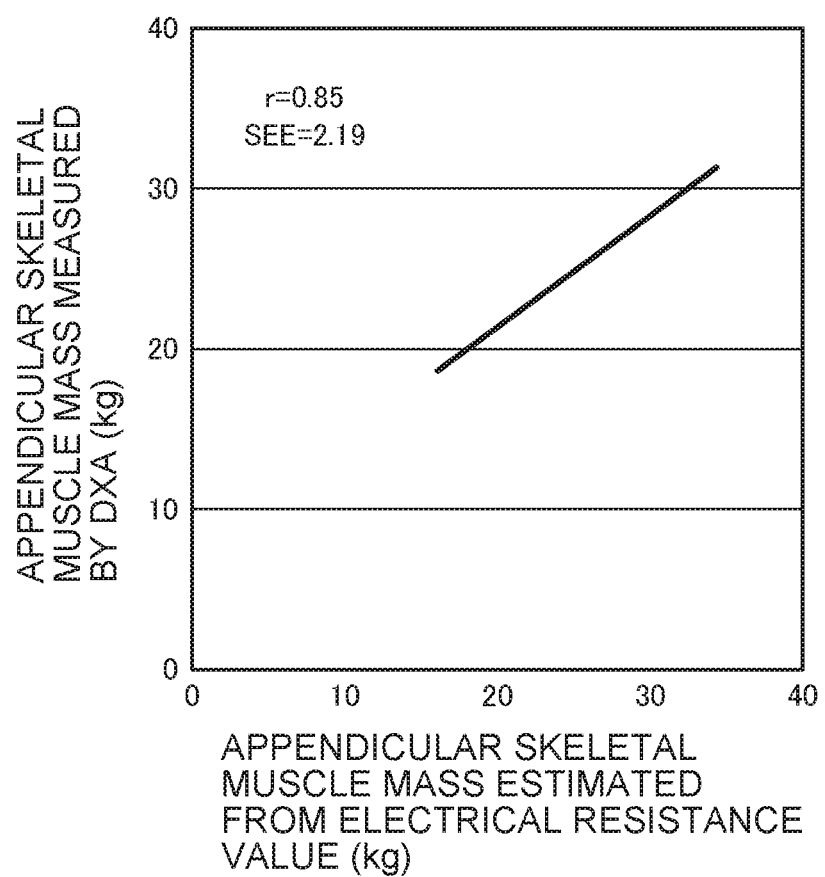
FIG. 9 is a graph illustrating a relationship between muscle mass calculated using a calculation formula only employing a first variable, and muscle mass measured by DXA.

FIG. 9 illustrates a relationship between the muscle mass computed using Formula A, namely, appendicular skeletal muscle mass estimated from the electrical resistance value), and appendicular skeletal muscle mass measured by dual energy X-ray absorptiometry (DXA). As illustrated in FIG. 9, the correlation r is 0.85 and the standard error SEE is 2.19.

Figure 10:
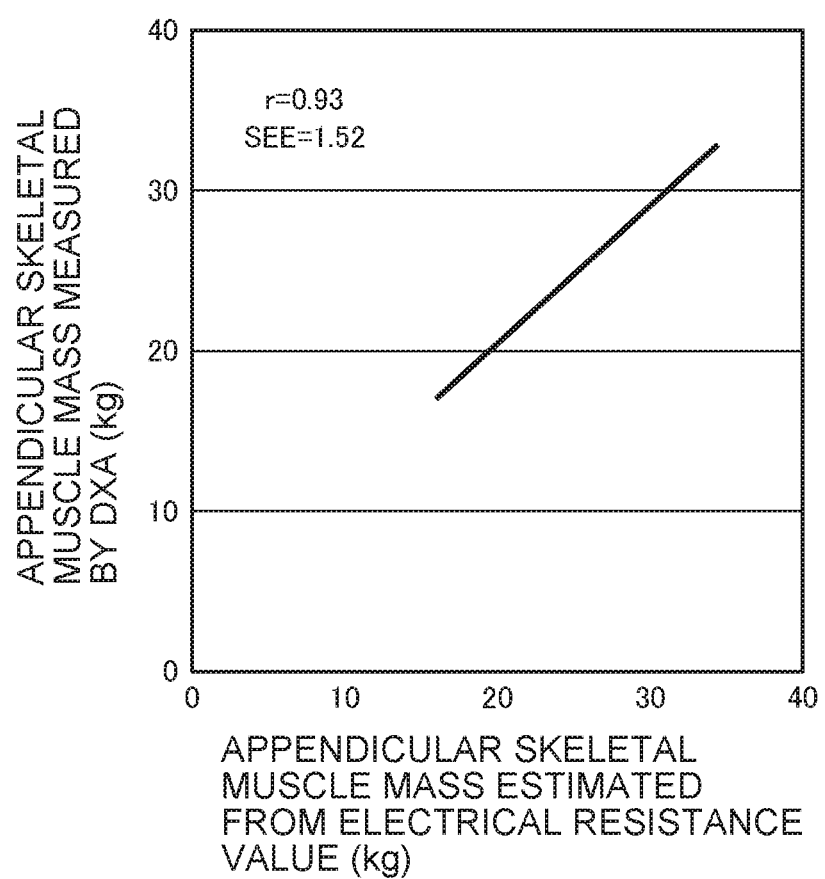
FIG. 10 is a graph illustrating a relationship between muscle mass calculated using a calculation formula employing a first variable and a second variable, and muscle mass measured by DXA.

FIG. 10 illustrates a relationship between muscle mass computed using Formula B and appendicular skeletal muscle mass measured by DXA. As illustrated in FIG. 10, the correlation r is 0.93 and the standard error SEE is 1.52.

Thus, it can be seen that both the correlation r and standard error SEE are superior in cases in which the muscle mass is computed using Formula B that additionally employs the second variable X2 to those in cases in which the muscle mass is computed using the first variable X1 alone.

Figure 11:
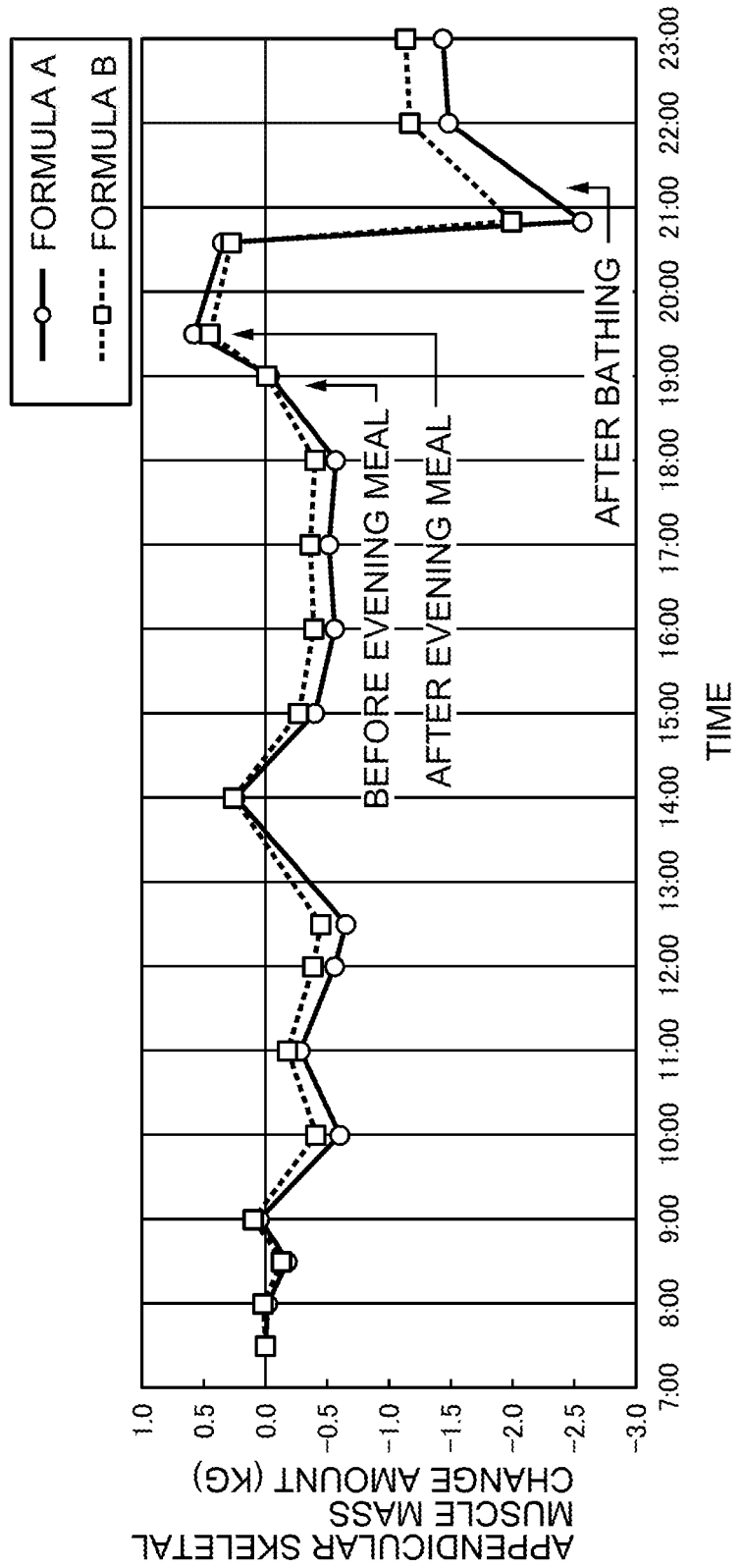
FIG. 11 is a graph illustrating a diurnal fluctuation amount in muscle mass.

FIG. 11 is a graph illustrating an example of diurnal fluctuation amounts in the muscle mass of the test subjects when computed using Formula A and diurnal fluctuation amounts in the muscle mass of the test subjects when computed using Formula B. In FIG. 11, the amount of change in muscle mass is illustrated using the muscle mass measured at 7:30 in the morning as a reference value.

As illustrated in FIG. 11, the largest change in muscle mass occurred after bathing, both when the muscle mass was computed using Formula A and when the muscle mass was computed using Formula B.

Specifically, the change in muscle mass was −2.6 (kg) when the muscle mass was computed using Formula A, whereas the change in muscle mass was −2.0 (kg) when the muscle mass was computed using Formula B.

Thus, it is clear that computing the muscle mass using Formula B employing both the first variable X1 ($Ht^2/Z$) and the second variable X2 better suppresses fluctuations in the amount of change in muscle mass than when the muscle mass is computed using the first variable X1 alone.

Note that although in the present exemplary embodiment, the Equations 9, 10, 11, and 12 were given as examples of calculation formulae for computing the muscle mass ASM, for example, alternative calculation formulae in which the sign of the first variable X1 and the sign of the second variable X2 are reversed may be employed. Specifically, Equations 9A, 10A, 11A, and 12A below may be employed instead of the Equations 9, 10, 11, and 12.

$$ASM = a + b \times (-Ht^2/Z) + c \times (1/Z) \tag{9A}$$

$$ASM = a + b \times (-Ht^2/Z) + c \times (-Z) \tag{10A}$$

$$ASM = a + b \times (Z/Ht^2) + c \times (1/Z) \tag{11A}$$

$$ASM = a + b \times (Z/Ht^2) + c \times (-Z) \tag{12A}$$

What is claimed is:

1. A muscle mass estimation method, comprising:
acquiring a body height of a living organism;
supplying a current to a body of the living organism and acquiring an electrical resistance value measured relative to the living organism based on the current supplied to the body of the living organism; and
computing a muscle mass of the living organism using a calculation formula that includes a first variable including the body height of the living organism and the electrical resistance value, and a second variable including the electrical resistance value, wherein the second variable is a variable that acts in a direction to suppress fluctuation in a computed value correlated with the muscle mass, and the computed value is computed by a term including the first variable in the calculation formula.

2. The muscle mass estimation method of claim 1, wherein:
in cases in which the electrical resistance value included in the first variable and the electrical resistance value included in the second variable are both included in a denominator or both included in a numerator, a sign of the second variable is opposite to a sign of the first variable; and
in cases in which one of the electrical resistance value included in the first variable or the electrical resistance value included in the second variable is included in a denominator and the other of the electrical resistance value included in the first variable or the electrical resistance value included in the second variable is included in a numerator, a sign of the second variable is the same sign as a sign of the first variable.

3. The muscle mass estimation method of claim 1, wherein:
a part of the first variable is a square of the body height divided by the electrical resistance value;
a part of the second variable is a reciprocal of the electrical resistance value; and
a sign of the first variable is opposite to a sign of the second variable.

4. The muscle mass estimation method of claim 1, wherein:
a part of the first variable is a square of the body height divided by the electrical resistance value;
a part of the second variable is the electrical resistance value; and
a sign of the first variable is the same as a sign of the second variable.

5. The muscle mass estimation method of claim 1, wherein:
a part of the first variable is configured by the electrical resistance value divided by a square of the body height;
a part of the second variable is configured by a reciprocal of the electrical resistance value; and
a sign of the first variable is the same as a sign of the second variable.

6. The muscle mass estimation method of claim 1, wherein:
a part of the first variable is the electrical resistance value divided by a square of the body height;
a part of the second variable is the electrical resistance value; and
a sign of the first variable is opposite to a sign of the second variable.

7. The muscle mass estimation method of claim 1, further comprising:
acquiring a body weight of the living organism;
selecting the calculation formula from a plurality of different calculation formulae according to the body height and the body weight; and
computing the muscle mass of the living organism using the selected calculation formula.

8. The muscle mass estimation method of claim 1, further comprising:
outputting the computed muscle mass on a display.

9. The muscle mass estimation method of claim 1, further comprising:
arranging a plurality of electrodes on a biometric measurement device such that when the living organism contacts the biometric measurement device to be weighed each of the plurality of electrodes are in contact with a respective body part among a plurality of body parts of the living organism,
wherein
supplying the current to the body of the living organism includes supplying the current to the plurality of body parts of the living organism through the plurality of electrodes, and
acquiring the electrical resistance value measured relative to the living organism based on the current supplied to the body of the living organism includes acquiring the electrical resistance value measured relative to the living organism based on the current supplied to the plurality of body parts of the living organism.

10. A muscle mass estimation device, comprising:
a height acquisition section that acquires a body height of a living organism;
a current supply section that supplies current to a body of the living organism;
an electrical resistance value acquisition section that acquires an electrical resistance value measured relative to the living organism based on the current supplied to the body of the living organism by the current supply section; and
a computation section that computes a muscle mass of the living organism using a calculation formula including a first variable including the body height of the living organism and the electrical resistance value, and a second variable including the electrical resistance value, wherein the second variable is a variable that acts in a direction to suppress fluctuation in a computed value correlated with the muscle mass, and the computed value is computed by a term including the first variable in the calculation formula.

11. A non-transitory storage medium stored with a muscle mass estimation program that, when executed by one or more processors of a computer, causes the computer to perform operations comprising:
acquiring a body height of a living organism;
supplying a current to a body of the living organism and acquiring an electrical resistance value measured relative to the living organism based on the current supplied to the body of the living organism; and
computing a muscle mass of the living organism using a calculation formula that includes a first variable including the body height of the living organism and the electrical resistance value, and a second variable including the electrical resistance value, wherein the second variable is a variable that acts in a direction to suppress fluctuation in a computed value correlated with the muscle mass, and the computed value is computed by a term including the first variable in the calculation formula.

\* \* \* \* \*